Dec. 27, 1949. R. ENGLE Plant Pat. 909
CARNATION PLANT
Filed June 14, 1948
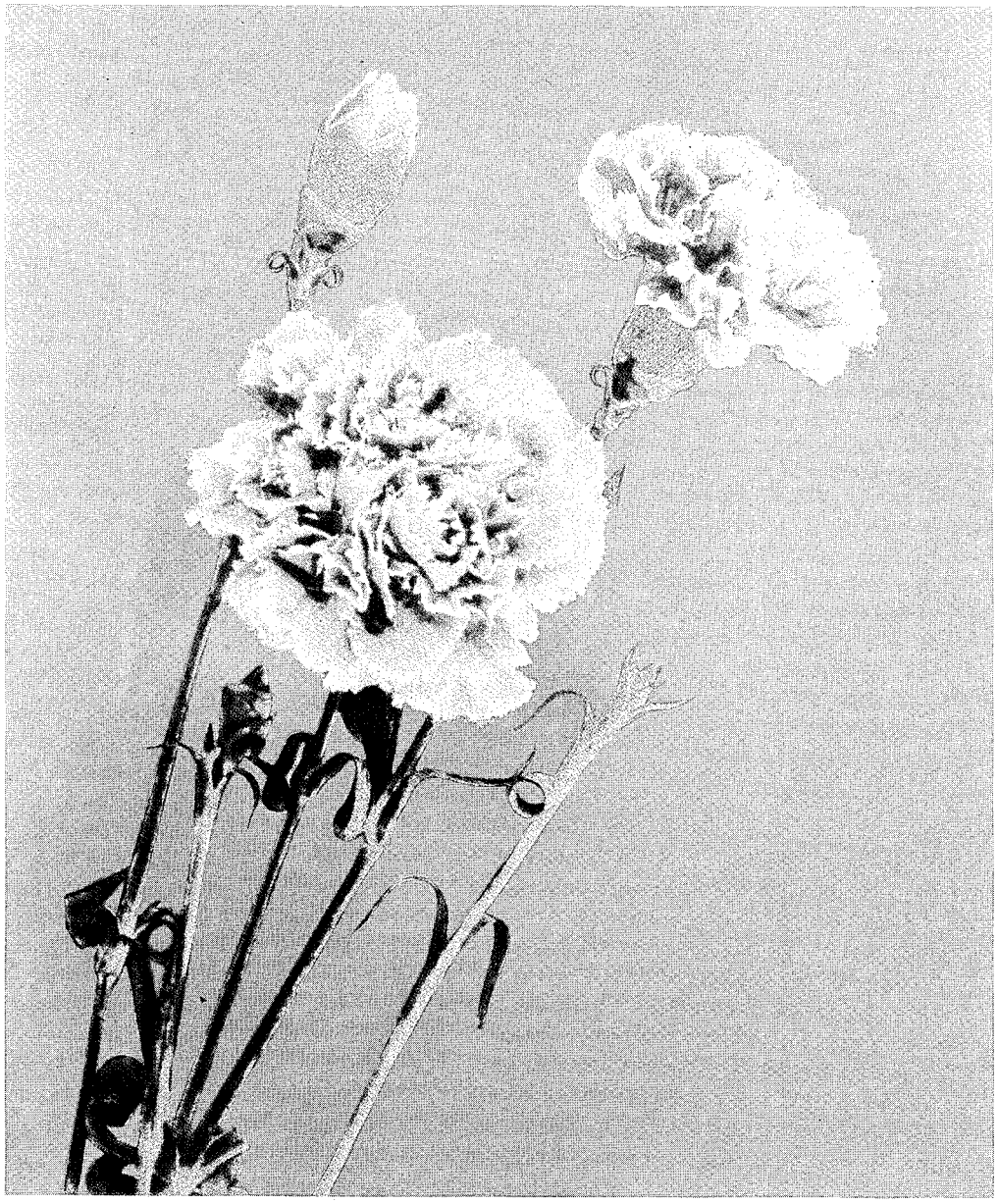
Inventor
Russell Engle
By Robert Cobb
attorneys Patented Dec. 27, 1949

Plant Pat. 909

UNITED STATES PATENT OFFICE

909

CARNATION PLANT

Russell Engle, Kokomo, Ind., assignor to Tom Knipe Florist, Kokomo, Ind., a partnership composed of Morna H. Knipe and Russell Engle Application June 14, 1948, Serial No. 32,871

1 Claim. (Cl. 47—60)

The present invention relates to a new and distinct variety of carnation plant of the greenhouse type and is the result of definite breeding efforts having as their objective the production of larger and better blooms in a wider range of color than exists in carnations now known to the trade.

This new variety was produced by crossing two unnamed lavender color seedlings grown by me in the greenhouse, and while its stem, foliage and general characteristics are similar to present existing varieties, the flower, itself, is very outstanding and distinct from all others of which I am aware. Its value as a commercial plant is indicated by the fact that the plants grow well in the field and equally well when kept inside during the summer season, and the color of the blooms is one that combined well with other colors, making it highly desirable to all floral design artists. In comparison with other varieties, there is, to my knowledge, no other variety color or color combination that comes close to the Rhodamine Purple color of this new carnation.

This new variety is also characterized by its prolific growth and branching habit, thereby conducing to high production of blossoms, so desirable in connection with greenhouse plant varieties.

Asexual reproduction of this new variety shows the foregoing characteristics come true to form and are established.

In the drawing (original) are illustrated specimens of this new variety of carnation, showing the flower at different stages of development from bud to full blown bloom in actual size. This new variety was asexually reproduced at Kokomo, Indiana, by cuttings.

The following is a detailed description of the new variety, color terminology being in accordance with Ridgway's Color Standards and Nomenclature:

*Plant*

Growth habits: Strong root growth; free branching from the base of the plant; medium in height, averaging three feet; roots easily and propagates readily.

Blooming habits: Early and consistent in producing good quality blooms throughout the winter season.

Stem: Straight and amply strong to hold the blossom erect; internodes average 3½ inches in length and are the same color as the foliage.

Foliage: Ample but not grassy; curled; averages four inches long and five-sixteenths inches wide.

*Color.*—Ackermann's Green, Plate XVIII.

*Flower*

Bud: Medium in size; one inch in length and five-eighths inches in width.

*Color.*—Slightly deeper than in the full open flowers, as herein described.

*Calyx.*—Single tube with five lobes; does not split. Color—Rinnemann's Green, Plate XVIII, fading to Mineral Green, Plate XVIII, at the very edges.

Bloom:

*Form.*—High centered and tightly bunched.

*Color.*—Base color of petals Rhodamine Purple, Plate XII, fading to Mallow Purple, Plate XII, and somewhat lighter at the very edges.

*Size.*—Medium, measuring from 2¾ inches to 3¼ inches in diameter.

*Petalage.*—Usual petalage 45 to 50 petals.

Petals:

*Texture.*—Good; laciniated or fringed; average 1¾ inches long from calyx to tip; ¾ inch wide at broadest point.

*Fragrance.*—Slight cinnamon.

*Lasting qualities.*—Above average.

*Bracts.*—Medium size; strong; same size as calyx.

*Reproductive organs*

Ovaries: Medium in size; about ¾ inch high.

Pistils: Four in number; white and slightly curled at the tip; average one inch in length, seldom visible above the petals.

Stamens: Four or five.

Filaments: About the same color as the petals and about the same length as the pistils.

Anthers: Same color as filaments; medium in size.

*Comparison*

The nearest similar variety to that of the present disclosure is found in prior Plant Patent No. 193 directed to the Rhodamine Purple Carnation known as "Orchid Beauty." The novel characteristics of this new variety are found primarily to reside in its unusual color, free flowering, disease resistance, and its ability to produce in great abundance throughout a long season. It is to be distinguished from the prior "Orchid Beauty" variety by the following features, taken either singly or in combination:

While the two varieties are similar in respect to the general color of Rhodamine Purple, this new variety is far superior in quality, color, growth and substance to that of "Orchid Beauty" and is distinct therefrom in every respect. More specifically, the carnation herein disclosed has a much higher center and perfect form as compared with that of "Orchid Beauty" which is rather flat and the outer petals of which have a tendency to curl. This new variety has a lasting quality which constitutes one of its main distinctions. The blooms last twice as long as those of "Orchid Beauty" and they dry to a crisp. The color of "Orchid Beauty" fades to almost white, while the color of the new variety retains its high color characteristic. It is notable that in "Orchid Beauty" there is no uniformity of the color and there is a tendency of the buds to blast or develop bull heads, while the growth is very long and lanky.

I claim:

A new and distinct variety of carnation plant characterized as to novelty by the unique color of its blossoms, combined with its prolific growth and branching habit, its strong root growth and its adaptability for growing outdoors as well as indoors, substantially as shown and described.

RUSSELL ENGLE.

REFERENCES CITED

The following references are of record in the file of this patent:

UNITED STATES PATENTS

| Number | Name | Date |
|---|---|---|
| Pl. Pt. 193 | Hemmings | Sept. 15, 1936 |